(12) United States Patent
Nummila et al.

(10) Patent No.: US 7,259,555 B2
(45) Date of Patent: Aug. 21, 2007

(54) METHOD FOR DETERMINING THE HARDENING DEPTH OF STEEL

(75) Inventors: Kaj Nummila, Espoo (FI); Heikki Seppä, Helsinki (FI); Timo Varpula, Vantaa (FI)

(73) Assignee: Stresstech Oy, Vaajakoski (FI)

( * ) Notice: Subject to any disclaimer, the term of this patent is extended or adjusted under 35 U.S.C. 154(b) by 165 days.

(21) Appl. No.: 10/525,457

(22) PCT Filed: Jan. 9, 2003

(86) PCT No.: PCT/FI03/00639

§ 371 (c)(1),
(2), (4) Date: Feb. 24, 2005

(87) PCT Pub. No.: WO2004/021024

PCT Pub. Date: Mar. 11, 2004

(65) Prior Publication Data

US 2005/0242803 A1    Nov. 3, 2005

(30) Foreign Application Priority Data

Sep. 2, 2002 (FI) ................................. 20021565

(51) Int. Cl.
*G01B 7/24* (2006.01)
*G01R 33/12* (2006.01)

(52) U.S. Cl. ............... 324/209; 324/232; 73/779; 73/862.69

(58) Field of Classification Search ............... 324/209, 324/228, 239, 226, 232; 73/862.69, 779
See application file for complete search history.

(56) References Cited

U.S. PATENT DOCUMENTS

| | | | |
|---|---|---|---|
| 3,697,866 | A | 10/1972 | Kanda et al. |
| 4,881,030 | A | 11/1989 | Stuecker et al. |
| 5,166,613 | A | 11/1992 | Perry |

FOREIGN PATENT DOCUMENTS

| | | |
|---|---|---|
| DE | 3037932 A1 | 4/1982 |
| EP | 531042 A | 3/1993 |

OTHER PUBLICATIONS

Dubois et al. "Evaluation of case depth on steels by Barkhausen noise measurement", Material Science and Technology, Mar. 1995, vol. 11, pp. 264-267.

*Primary Examiner*—Bot LeDynh
(74) *Attorney, Agent, or Firm*—Birch, Stewart, Kolasch & Birch, LLP

(57) ABSTRACT

This publication discloses a method and arrangement for determining the hardening depth of steel or other ferromagnetic substances without breaking the object being measured. According to the invention, a varying magnetic field, which causes magnetic Barkhausen noise (MBN), is created in the measurement object with the aid of a magnetization coil 13. The varying magnetic field is regulated in such a way that the maximum force of the magnetic field does not exceed the coercive force of the unhardened part of the measurement object. The MBN caused is measured with the aid of an MBN sensor. The measured signal is filtered and Fourier transformed. The signal in the frequency range is integrated over a suitable frequency band, in order to determine the value depicting the energy of the MBN. This value correlates with the hardening depth and on the basis of this value it is thus possible to determine the hardening depth.

22 Claims, 4 Drawing Sheets

METHOD FOR DETERMINING THE HARDENING DEPTH OF STEEL

The present invention relates to a method, according to the preamble of claim 1, for determining the hardening depth of steel. In addition, the invention relates to an arrangement, according to claims 11, for determining the hardening depth of steel.

Methods and arrangements of this kind are used to determine the hardening depth of steel products, such as steel axles and plates.

The greatest mechanical stresses in materials and components act on their surface layers. There are several methods in use for increasing the hardness of the surface and the adjacent area, for example, the various methods for tempering steel. The methods according to the prior art for determining the hardening depth of steel require machining that damages the piece and are thus expensive and time-consuming. The prior art also includes so-called NDE (Non Destructive Evaluation) methods, by means of which the hardening depth of production pieces can be measured more rapidly and without breaking the material. Such NDE methods are disclosed, for example, in the following publications:

EP 0 100 009

'Characterization of Hardening Depth by Barkhausen Noise Measurement', G. Bach, K. Goebbels, & W. A. Theiner, Materials Evaluation 46, 1988, The American Society for Nondestructive Testing Inc.

'Evaluation of case depth on steels by Barkhausen noise measurements', M. Dubois & M. Fiset, Materials Science and Technology Vol. 11, 1995.

'Evaluation of Induction Hardened Case Depth Using Magnetic Barkhausen Emission', S. Vaidyanathan, V. Moorthy, T. Jayakumat, & Baldev Raj, Indira Gandhi Center for Atomic Research, 1998.

Extensive research has been carried out on the applicability of magnetic Barkhausen noise (MBN) to NDE measurements relating to the metallurgical, mircrostructure, and mechanical properties of ferromagnetic materials. The research has concentrated on measuring the change in MBN caused by the internal properties of materials, in order to be able to find commercially exploitable correlations between material properties and MBN. Barkhausen noise has been observed to depend on such factors as the grain size of a ferromagnetic material, its composition, and its pearlitic and lamellar structures. In steel, an important factor relating to composition is the amount and distribution of carbon. Of mechanical properties, at least hardness, residual stress, and material fatigue have been shown to affect MBN.

The physical basis of the measurement of Barkhausen noise is the fact that, for example, the factors, such as microstructure, composition, and crystalline faults that affect hardness also strongly affect the magnetic properties of materials, such as the shape of the hysteresis curve, the coercitive force, and remanence. A ferromagnetic piece comprises elementary domains, i.e. so-called Weiss's domains, in which all the elementary magnets have the same direction. When the piece is magnetized, the magnetization increases with small field strengths as a result of the increase in the size of the elementary domains parallel to the field and approaches saturation magnetization as the magnetization of more and more elementary domains rotates to the direction of the external field. Material faults tend mainly to limit the movement in the material of the Bloch walls relating to the growth of the elementary domains. As the strength of the magnetic field increases, the Bloch walls receive sufficient energy to be released from the crystal faults and impurities and magnetization increases in jumps. The measurement of magnetic Barkhausen noise is based on measuring these sudden, irreversible magnetization changes, with the aid of the changes in the magnetic flow detectable on the surface of the piece. In the vicinity of a coercitive force, the magnetization changes rapidly, in which case a great deal of MBN arises.

According to the prior art, a magnetic field that causes MBN, and which changes according to a sine curve, is induced in the measurement object. The magnetic field is typically induced using a magnetization coil, which has typically a U-shaped ferro- or ferrimagnetic core, the points of which touch the measurement object. The MBN created is typically measured using a magnetometer, which is placed between the points of the core of the magnetization coil and in contact with the surface of the measurement object. The magnetometer is typically set in such a way that its windings are essentially parallel to the contact surface of the measurement object. The MBN and hardening depth are determined on the basis of the voltage induced in the magnetometer. Most of the Barkhausen noise arises when the strength of the magnetic field is close to the material's specific coercitive force. When measuring the hardening depth of steel with the aid of MBN, it is important to distinguish between the Barkhausen noise arising in the hardened and the unhardened zones. In the prior art, two methods are used. Both methods use a magnetizing field large enough to achieve the saturation magnetization of the sample. In the first method, the voltage caused by the MBN is measured as a function of the strength of the magnetization field. If the coercitive forces of the hardened and unhardened steel layers differ sufficient from each other, two separate peaks can be distinguished in the measurement data, the ratio of the maximum amplitude of which is used to determine the hardening depth. The coercitive force of the mechanically more hardened layer is generally greater than that of the unhardened material, so that the noise peak appearing at the strength of the more powerful magnetic field relates to the hardened layer. Generally, clearly less Barkhausen noise arises in hardened steel that in unhardened. In the second method, the lower limit of the frequency band of the measurement is selected so that the noise coming from the unhardened zone inside the material is attenuated in this frequency range to be undetectable. This lower limit of the frequency band set using a filter corresponding to this situation to determine the hardening depth.

A drawback of the state of the art is that, in the first method, the noise of the hardened zone is also measured, as this has a central role in determining the hardening depth. Thus, the measurement results are also affected by variations in properties unrelated to the hardening depth, such as the surface tension of the material and possible variations in the carbon content, for example, carbon depletion zones. Demagnetization fields and the closing of elementary domains may have a greater effect than the microstructure of the material on the dynamics of the elementary domains of the surface layer. In addition, the first method will only work, if the noise peaks created by the different zones are far enough from each other for their amplitudes to be reliably determined. The second method is fairly inaccurate, as it is based on deleting a weak noise signal. This cannot be done precisely and the method is hardly used at all.

The strength $H(x)$ of a magnetic field varying with a frequency f is attenuated, in a homogenous electrically conductive magnetic material, from its initial value H(0) as the distance x increases, roughly as follows:

$$H(x)=H(0)\exp(-x/\delta); \delta=\sqrt{1/(\pi f \mu \sigma)},$$

where δ is the depth of penetration, μ is the permeability of the magnetic material, and σ is the electrical conductivity. The magnetizing field should penetrate sufficiently deeply into the sample being examined, in order that MBN will be created also in the deeper unhardened layer. For this reason, a low frequency is used in magnetization. Also, the MBN arising in the unhardened layer is attenuated exponentially as a function of the hardening depth, so that, when measuring great hardening depths, a low-frequency measuring band must be used. Some measurements using the prior art have been made using analysis frequencies high enough for the measured MBN to come from only the surface layer.

The invention is intended to create an entirely new type of method for determining the hardening depth of steel, by means of which the hardening depth of steel can be measured more accurately and to a greater hardening depth than when using the prior art.

The invention is based on a new way of magnetizing and on processing the measurement results in a new way. As a result of these, the sensitivity of the method to variations in factors that are independent of the hardening depth, but which alter the MBN, is reduced considerably, the measurement accuracy improves, and measurements can be made to a greater hardening depth.

A variable magnetic field, which causes MBN, is formed in the measurement object, in such a way that the noise to be measured arises mainly in the unhardened zone and the MBN caused is measured using a sensor according to the prior art. The sample is thus not magnetized to close to the saturation magnetization. The measured MBN is converted, for example with the aid of FFT (Fourier Fast Transform) to the frequency level and the value depicting the energy of the measured MBN is determined, for example, by integrating the measured MBN over a suitable frequency band in the frequency level. Finally, on the basis of the value depicting the energy of the MBN, the hardening depth of the measurement object in determined. Before determining the hardening depth, the electronics' own background noise, measured with a null magnetization current, is deducted from the measured noise.

The hardening depth can be determined, for example, using a previously created table or formula, which is determined with the aid of test measurements. In the test measurements, the correlation between the value depicting the energy of the MBN and the hardening depth can be determined for a specific product, such as a steel plate. The test measurements can be performed, for example, by first using the method according to the invention to measure the values depicting the energy of the MBN in a test batch of products, and then using, for example, some mechanical method to measure the hardening depths of the products at corresponding points. The products should have different hardening depths and the test batch should be sufficiently large for the correlation curve to be reliable.

The lower limit of the integrating frequency band is set as close as possible to the frequency of the varying magnetic field induced in the measurement object, i.e., for example, between 1 and 200 Hz, because only at sufficiently low frequencies is information obtained beneath the hardened layer. The upper limit of the integrating frequency band, on the other hand, is set in such a way that no more of the higher frequency MBN, coming from the surface layer of the measurement object, than is essential is included in the integration.

More specifically, the method, according to the invention, for measuring the hardening depth of steel, is characterized by what is stated in the characterizing portion of claim 1.

More specifically, the arrangement, according to the invention, for measuring the hardening depth of steel, is characterized by what is stated in the characterizing portion of claim 11.

Considerable advantages are gained with the aid of the invention.

With the aid of the method according to the invention, the hardening depth of steel can be measured more accurately than by using the methods according to the prior art.

In preferred embodiments, the magnetization current of the magnetization coil is adjusted in such a way that the strength of the magnetic field exceeds the coercitive force of the unhardened steel, but does not exceed the coercitive force of the hardened part. In other words, the strength of the magnetic field does not exceed the coercitive force of the hardened surface layer, but does exceed the coercitive force of the unhardened steel beneath the hardened surface layer. If the strength of the magnetic field does not exceed the coercitive force, the irreversible changes in the walls of the elementary domains will be considerably fewer than when the magnetic field exceeds the coercitive force. Correspondingly, MBN will be less, if there are smaller and fewer changes in the size of the elementary domains. In addition, at low field strengths, the magnetization changes are reversible, in which case Barkhausen noise will not arise. This makes it possible to reduce MBN caused by properties unrelated to the degree of hardness of the surface layer. Such properties include surface tension and variations in carbon content. As a result, less inessential MBN, which reduces the correlation of the measurement and is unrelated to the hardening depth, will be connected to the measurement magnetometer, thus improving the measurement accuracy. Measurement accuracy will also be improved by the hardening depth being determined with the aid of the total energy of the MBN coming from the unhardened zone and not only on the basis of the amplitude of the noise peak, as in the prior art.

In preferred embodiments, the sampling frequency of the FFT transformation and the magnetization frequency are synchronized with the power-supply network frequency. As a result of the synchronization, the signals can be measured at a time that is a multiple of both disturbances and their harmonic components. Thus the disturbance peaks are ideally narrow, i.e. they contain only one point in the frequency range and can be easily removed from the frequency spectrum. Due to this, the analysis frequency range can start relatively closer to the magnetization frequency than in measurements according to the prior art, thus improving the measurement accuracy and permitting measurement of greater hardening depths.

The term magnetization frequency refers to the frequency of the varying magnetic field induced by the magnetization coil. The term power-supply network frequency, in turn, refers to the frequency of the electrical power network in the vicinity of the measurement equipment, i.e. generally the frequency of the national grid, which is typically 50 or 60 Hz. The term sampling frequency refers to the number of samples picked from the measurement data in a unit of time. If the sampling frequency is, for example, 100 Hz, a measurement value corresponding to the moment in time t seconds, a measurement value corresponding to the moment in time (t+1/100) s, a measurement value corresponding to the moment in time (t+2/100) s, etc.

In the preferred embodiments, the upper limit of the measurement band is also set to a level, at which possible variations in the properties of the surface layer will cause the least possible error in the result of hardening depth measurements. The measurement frequency band can be, for example, 100-1200 Hz.

At higher frequencies, the magnetic field of the magnetization coil is squeezed closer to the surface of the measurement object, so that the magnetic field reaching the unhardened layer will be weaker and thus the MBN caused will be less. For example, at a frequency of 50 kHz, the penetration depth in steel is only about 60 μm. Therefore, in the preferred embodiments, the magnetization frequency is set to be low, for example, between 0.1 and 10 Hz, so that the magnetic field will penetrate sufficiently deeply into the steel being examined, i.e. to the unhardened layer. At low magnetization frequencies, the magnetization flux connected to the measurement magnetometer is smaller. Thus it is easier to filter out of the voltage induced in the measurement magnetometer the magnetization frequency signal caused by the magnetization coil and the signals of the multiples of the magnetization frequency. The Barkhausen noise also diminishes, however, rather rapidly, as the magnetization frequency is reduced. This is explained as being due to the fact that the number of Bloch's walls in the piece, participating in the magnetization process at a specific current density, is proportional to the square root of the magnetization frequency. As the number of walls between the elementary domains decreases, the Barkhausen noise also decreases. For these reasons, in the preferred embodiments, a sensor optimized for low frequencies and low-noise preamplification are used in the measurements. In order to maximize the signal-to-noise ration, the preamplifier is located in connection with the sensor.

In the preferred embodiments, the magnetic properties of the unhardened and hardened material of the object, such as the magnitude of the coercive force, can, if necessary, be defined and the measurement arrangement tuned on this basis. In order to facilitate the adjustment of the strength of the magnetic field, a Hall sensor can be installed in the measurement sensor, which will measure the strength of the magnetic field parallel to the direction of the surface of the sample. The best value of the magnetic current can also be sought experimentally, without precise data on the coercive force of the material, or on the other magnetic properties. A coil sensor, which is wound around a magnetization core, and measures the magnitude of the magnetization flux and the magnetization flux density, is used to assist this. The value giving the best correlation with the hardening depth is selected as the final value of the magnetization current. The measurement of the hardening depth should be performed at such a stage in the processing of the products, in which there the difference between the hardened and unhardened parts is largest. Several samples should be used when calibrating and adjusting the measurement arrangement.

In the following, the invention is examined with the aid of examples and with reference to the accompanying drawings. The numerical values appearing in the text are indicative and refer to implemented solutions. Depending on the measurement object, the values of the said parameters may vary to a very much greater extent.

Figure 1:
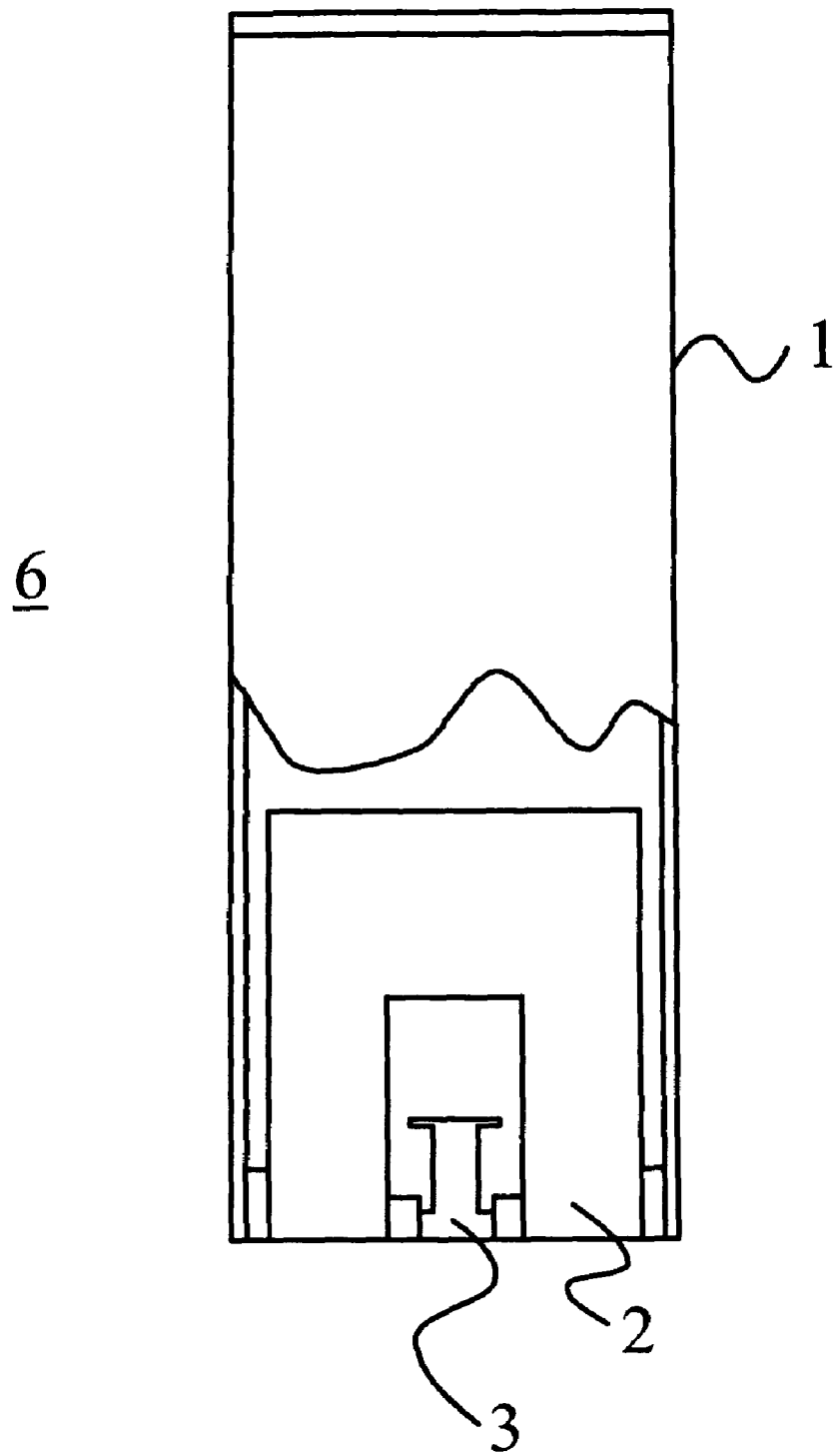
FIG. 1 shows a cross-section of a sensor, which can be used in the method and arrangement according to the invention.

The sensor 6 shown in FIG. 1 includes a protective casing 1, a magnetization core 2, and the core 3 of a magnetometer.

The dimensions of the magnetization core can, for example as follows:

| | |
|---|---|
| Overall height | 30 mm |
| Overall width | 25-34 mm |
| Thickness | 13-20 mm |
| Width between points | 8-12 mm |
| Height of the inner edge of the points | 17-18 mm |

Around the magnetization core, there are magnetization windings, which are not shown in the figure. The number of the windings can be, for example, 200-250, the diameter of the winding wire being, for example, 0.4-0.45 mm. The core of the magnetization coil can be, for example, Philips 3C80 ferrite, which has a permeability of about 2000. With the above dimensions, the resistance of the magnetization coil will then be about 2 –3Ω, when the frequency is 0-10 Hz. Around the magnetization core there are also windings measuring the magnetization flux, which are not shown in the figure. The windings of the flux coil can also be symmetrical, in order to reduce the level interference, for example, 10+10 windings at the intermediate output, which is connected to the earth potential of the electronics of the sensor.

The magnetometer is optimized for low frequencies. At low frequencies, the signal-to-noise ratio of the coil magnetometer increases in proportion to the amount of copper in the windings of the coil, so that the magnetometer is dimensioned to be relatively large. The core of the magnetometer can be, for example, 10-13 mm thick, 6-10 mm high, and 3-5 mm wide at its narrowest point. The number of windings of the magnetometer can be, for example 1000-4000, and the diameter of the winding wire, for example, 0,04-0,06 mm. The windings of the magnetometer are not shown in the figure. To reduce capacitive interference, the windings of the magnetometer are symmetrical and the intermediate output of the coil is connected to the earth potential of the electronics of the sensor. The core of the magnetometer should be low-noise, for example, Philips 3C80 ferrite. With the above dimensions, the resistance of the magnetometer will be about 100-400 Ω, the frequency being 0-1000 Hz.

Inside the casing, there is also a low-noise, differential preamplifier, by means of which the measurement signal is amplified. The preamplifier is not shown in FIG. 1. The low impedance of the measurement coil limits the choice of operational amplifiers that can be used in the preamplifier. In terms of background noise, the best match is achieved when the optimal noise impedance of the amplifier, i.e. the voltage and current noise of the equivalent, $Z_{opt}=e_n/i_n$ is equal to the impedance of the measurement coil. In the preamplifier, is it possible to use, for example, the AD797 operational amplifier manufactured by Analog Devices Inc., or the LT1028

Ultra Low Noise Precision High Speed Operational Amplifier manufactured by Linear Technology Inc. The preamplifier can be implemented by a differential instrumentation amplifier circuit, in which the calculated amplification of the differential input stage is, for example, 67 and that of the second stage is 50, so that the total amplification is about 3350. In order to limit the width of the measurement band, it is possible to implement a first-order band-pass filter, the −3 dB angular frequencies of which are about 146 Hz and 1300 Hz, between the amplification stages. The band-pass filter reduces the calculated amplification in such a way that the amplification in the middle of the pass band is about 2200. The voltage noise of the preamplifier can be about 2.0-4.0 nV/√Hz and the current noise about 7 −10 pA/√Hz. The total level of background noise on the measurement band can be 3.5 −5.0 nV/√Hz, if the proportion of noise of the measurement coil is about 1.5 nV/√Hz.

The measurement coil and the preamplifier must be designed in such a way that the voltage induced in the magnetometer by the magnetic field caused by the magnetization coil does not saturate the preamplifier, i.e. cause so-called cutting. Particular care must be taken not to connect the magnetization signal directly to the preamplifier.

The protective casing 1 also contains its own preamplifier for measuring the magnetization flux and the magnetization flux density. The measured signal is proportional to the time derivative of the flux, from which the effective flux value and the maximum value of the flux density are calculated by integration. Integration and calculation are performed numerically in the analysis program.

Figure 2:
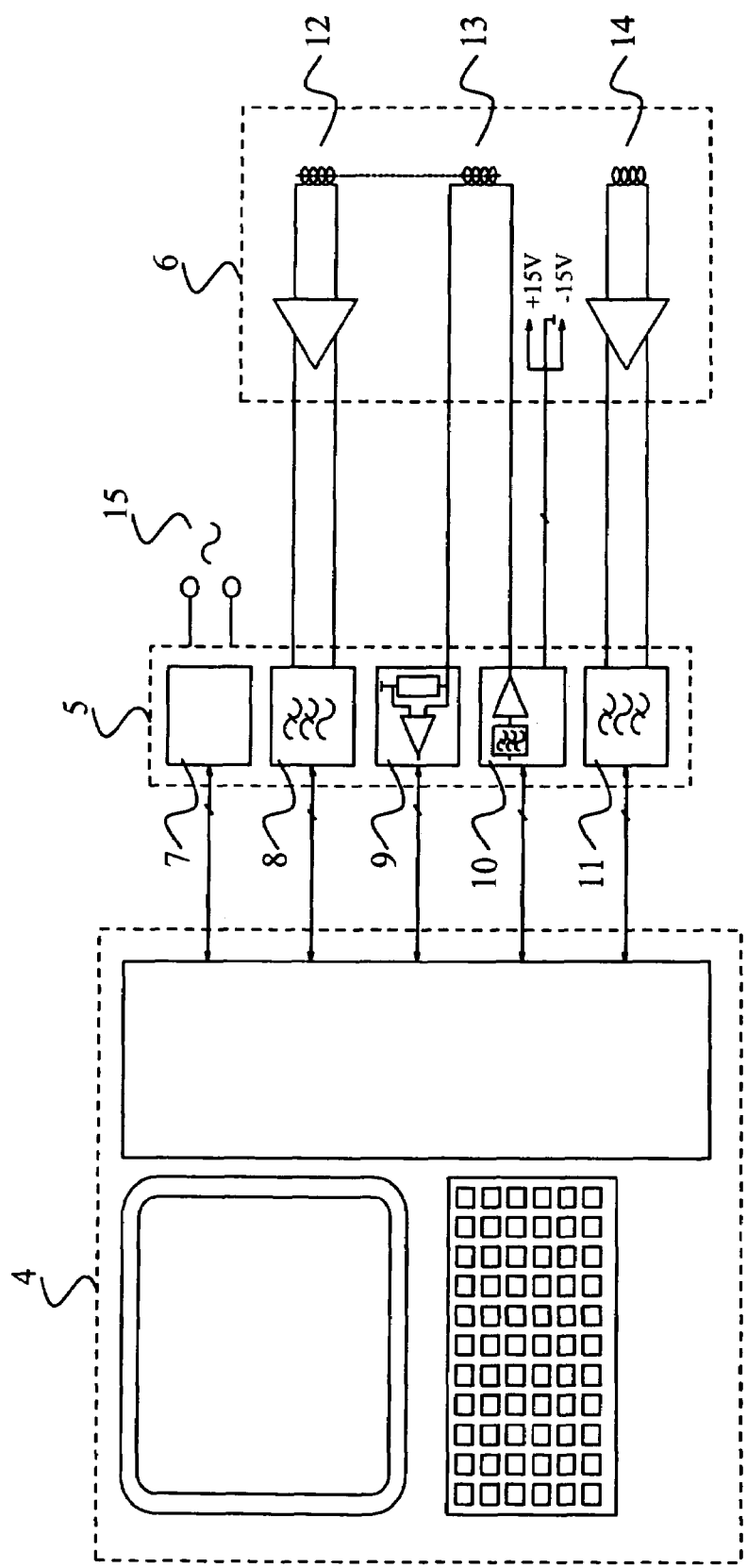
FIG. 2 shows a block diagram of the measurement arrangement according to the invention.

The arrangement according to FIG. 2 includes a PC computer 4, measurement electronics 5, and a sensor 6. The PC computer in turn includes a multi-channel A/D and D/A converter card and software, by means of which the measurement data can be FFT converted, edited, and analysed. The software can perform FFT transformation in the desired frequency range, remove the interference from the measurement data and calculate the quantities required to determine hardening depth. The measurement electronics further include a synchronization circuit 7, a magnetization current circuit 8, a magnetization current measurement circuit 9, a magnetization circuit 10, and an MBN measurement circuit 11. The sensor 6 further includes a sensor, with a preamplifier 12, measuring the magnetization flux, a magnetization coil 13, and an MBN sensor 14, which also includes a low-noise preamplifier.

The synchronization circuit 7 provides the computer's 4 A/D and D/A conversion card with a synchronizing signal, by means of which the clock circuits of the conversion card are synchronized with the frequency of the power-supply network 15. The synchronization circuit creates the synchronization signal from the mains voltage, with the aid of a PLL (Phase Locked Loop) circuit and a programmable distributor circuit. In addition, the control and measurement signals travel between the computer's 4 A/D and D/A conversion card and the measurement electronics 5 through the synchronization circuit 7.

The magnetization flux measurement circuit 8 receives a differential signal from the sensor 12 measuring the magnetization flux. The circuit converts the symmetrical signal into an asymmetrical signal, low-pass filters it to remove disturbances, and reconverts it to a symmetrical signal, which is fed to the computer's 4 A/D and D/A conversion card, through the synchronization circuit 7.

The magnetization current flowing through the magnetization coil in the magnetization current measurement circuit 9 is measure by leading the current through a quadripole resistance and measuring and amplifying the voltage created over the resistance.

The magnetization circuit 10 receives a sine signal from the computer's 4 A/D and D/A conversion card through the synchronization circuit 7, which is low-pass filtered, amplified, and, if desired, converted to be symmetrical, and led to the magnetization coil 13 of the sensor 6. If desired, the computer 4 can be used to regulate the magnetization current, with the aid of the measured magnetization current and the magnetization flux, in such a way that the amplitude of the magnetization flux is set to the desired constant value, independently of the measurement object. In addition, the magnetization circuit 10 feeds the necessary operating voltages required by the preamplifiers of the sensor 6.

The MBN measurement circuit 11 receives a symmetrical, differential signal relative to the earth potential of the electronics, from the MBN sensor 14. The signal is amplified and the circuit converts the symmetrical signal to an asymmetrical signal, low-pass filters and high-pass filters it to remove disturbances, and reconverts it to a symmetrical signal, which is fed to the computer's 4 A/D and D/A conversion card, through the synchronization circuit 7.

The sensor 12 measuring the magnetization flux 12 includes a measurement coil, which is wound around a magnetization core. The symmetrically measured differential signal is amplified by the preamplifier in the sensor 6 and fed as a differential signal to the magnetization flux measurement circuit 8. In the magnetization flux measurement circuit 8, the signal is again amplified, converted to be asymmetrical, and filtered with a low-pass filter. Finally, the signal is reconverted to be symmetrical and fed through the synchronization circuit 7 to the computer's 4 A/D and D/A conversion card.

The magnetization coil 13 and the MBN sensor 14 are in accordance with FIG. 1 and its description. The preamplifier of the MBN sensor 14 feeds the differential-form measurement signal to the MBN measurement circuit 11.

The entire apparatus 4-6 is protected as well as possible from disturbances, for example, with the aid of opto-isolation, earthing, and protection. In addition, all the signals are brought to the measurement electronics 5 in a form that is symmetrical relative to the earth potential of the electronics.

The measurement is performed, for example, as follows:

I. The measurement electronics 5 are controlled by the computer 4 in such a way that, for example, a 0.1-10 Hz-frequency sine-form constant amplitude magnetization current is induced in the magnetization coil. The magnetization current is regulated in such a way that the amplitude of the magnetic field formed in the steel piece of the magnetization coil does not exceed the coercitive force of the hardened part of the object being measured, but does exceed the coercitive force of the unhardened part of the object being measured.

II. The voltage signal induced in the magnetometer of the MBN sensor 14 is preamplified and band-pass filtered according to the desired measurement band and fed to the MBN measurement circuit 11. The MBN measurement signal is further low-pass filtered in order to remove high-frequency disturbances. Correspondingly, the signal is high-pass filtered in order to reduce low-frequency disturbances, such as disturbances induced in the magnetic field of the magnetization coil. After filtering, the measurement signal is converted to a differential form and fed through the synchronization circuit 7 to the computer's 4 A/D and D/A conversion card.

III. The computer 4 receives the signal sent by the MBN measurement circuit 11, from the synchronization circuit 7 and performs FFT transformation with the aid of its software. The sampling frequency and magnetization frequency of the transformation are synchronized with the frequency of the power network, with the aid of the signal obtained form the synchronization circuit.

IV. The FFT-transformed measurement data are integrated, for example, on the frequency band 100-1200 Hz, with the aid of the software of the computer 4.

V. Stages II.-IV. are repeated, for example, 10-100 times, keeping the sensor 6 at the same point on the piece being measured and the average value of the integration results of stage IV is determined.

VI. The average of the values obtained as a result of the integration depicts the energy of the MBN in the integrated frequency band and the hardening depth of the measurement object can be deduced on the basis of this value.

In the measurement, a good contact between the sensor and the piece being measured is important, as an air gap between the sensor and the measurement object can cause a measurement error, as a result of a different division of the flux. The measurement is hampered by vibration of the sensor arising from the magnetic force. The sensor can be secured to the sample with a clamp, to hold it in place during the measurement.

In the measurement, it is possible to use, for example, a resolution bandwidth of 0.52 Hz. The frequency resolution is selected in such a way that the lowest magnetization used is about 5-10 times the frequency resolution. In that case, the algorithm used to remove disturbance peaks will function well. The measurement data can also be processed using other kings of filtering and/or disturbance-removal algorithms.

A strong magnetization signal may cause disturbances below 100 Hz, on account of which the integration of stage IV can be calculated over the frequency band 100-1200 Hz.

Figure 3:
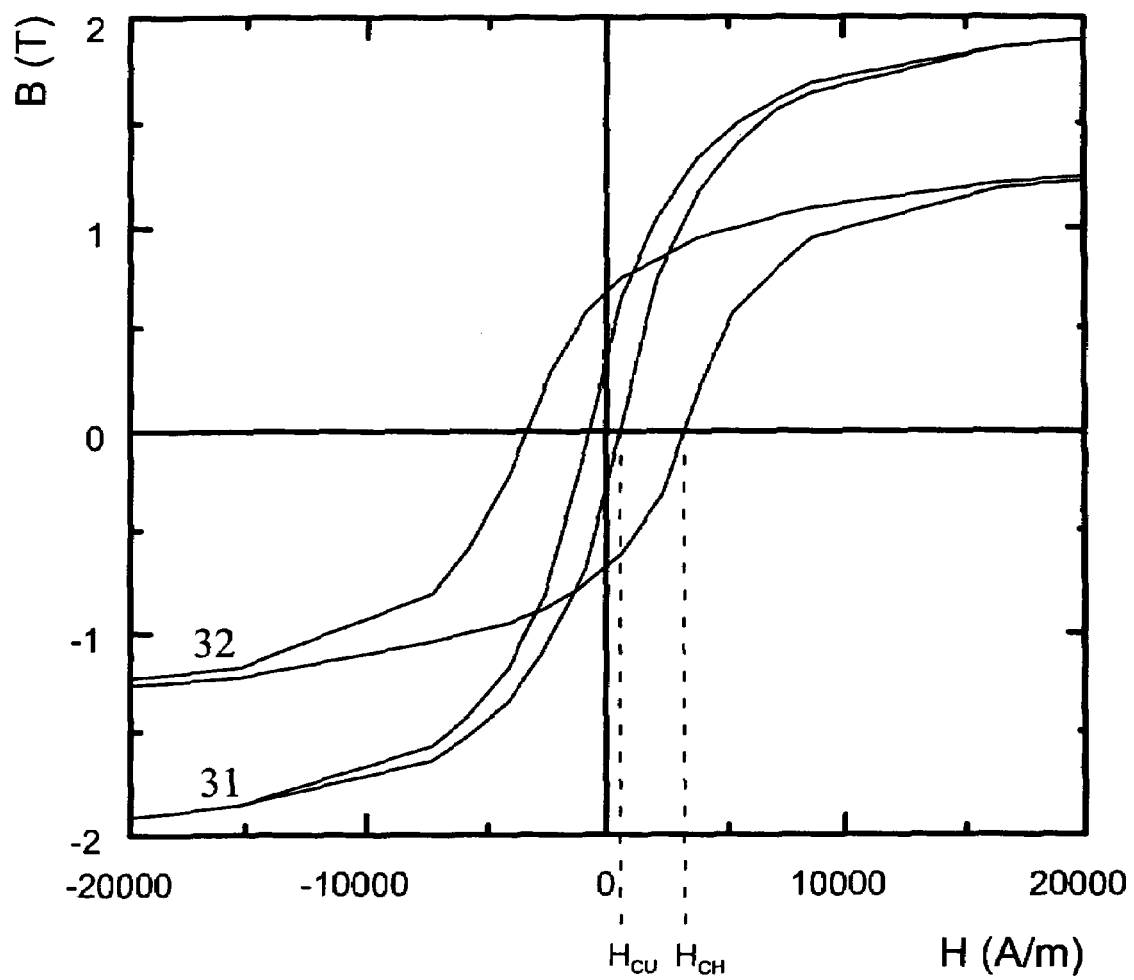
FIG. 3 shows part of the hysteresis curve of the hardened and unhardened parts of an example sample, on which the corresponding coercitive forces are marked.

FIG. 3 shows the hysteresis curves of the hardened and unhardened parts of an example sample. In the graph, the magnetic flux density B in the hardened and unhardened parts is shown as a function of the strength H of the magnetic field. Curve 31 is the hysteresis curve of the hardened part and curve 32 is the hysteresis curve of the hardened part. The coercitive force of the unhardened part is shown by the broken line $H_{CU}$ (Coercivity, Unhardened). The coercitive force of the hardened part is shown by the broken line $H_{CH}$ (Coercivity, Hardened). The term coercive force thus refers to the strength of the magnetic field that is required to demagnetize a ferromagnetic material that has been magnetized to saturation, i.e. to remove the magnetization. As can be seen from the graph, the rate of change of the magnetic flux density is greatest in the vicinity of the coercitive force, so that the most MBN arises in this area.

Figure 4:
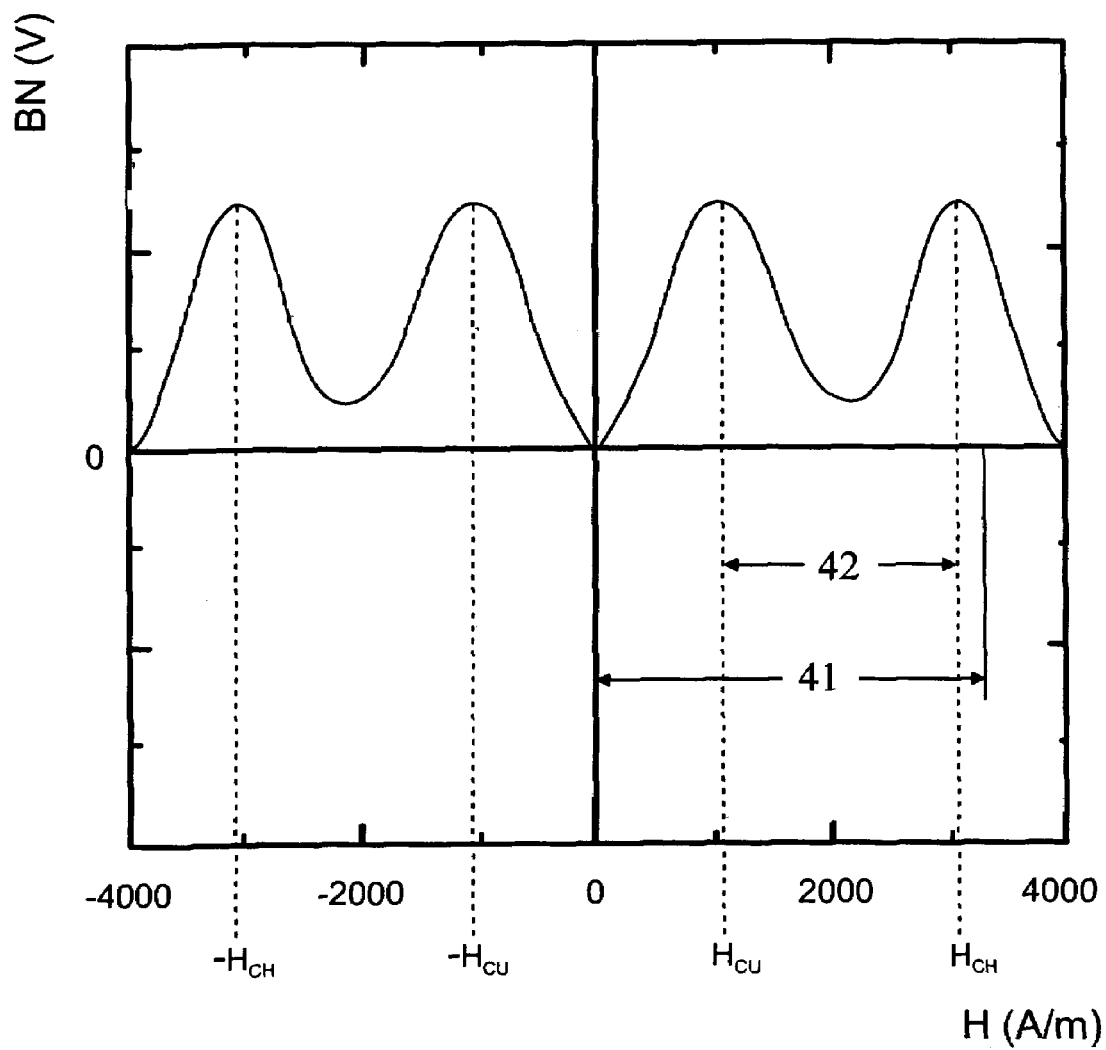
FIG. 4 shows a graph of MBN formed using saturation magnetization in a sample corresponding to the example sample of FIG. 3, in which the coercitive forces corresponding to those of FIG. 3 are marked, as well as example of magnetization intervals according to the invention.

FIG. 4 shows the MBN arising in a sample corresponding to the example sample of FIG. 3, when a varying magnetic field, which saturates the sample, is directed onto the sample. In the graph, the MBN is shown as a voltage (Barkhausen Noise) as a function of the magnetic field H. The graph is only indicative, the real curve may differ considerably from the curve of the figure. The MBN is greatest at the coercitive forces $H_{CU}$ and $H_{CH}$ of the unhardened and hardened parts, as at these points the magnetic flux density changes greatly. According to the invention, the object an attempt is made to magnetize the object in such a way that the greatest possible part of the MBN caused comes from the unhardened part. In other words, the varying magnetic field causing the MBN is regulated in such a way that more MBN arises in the unhardened part of the object than in the hardened part. Thus a value, which is at most 110% of the value of the coercitive force of the hardened part is selected as the maximum magnitude of the varying magnetic field, in which case most of the MBN caused will come from the unhardened part. This maximum strength is thus selected from the interval 41 shown in the figure. In other words, the varying magnetic field is set to vary, for example, between —$H_{CH}$—$H_{CH}$. In preferred embodiments, the maximum strength of the varying magnetic field is set between the coercitive force $H_{CU}$ of the unhardened part and the coercitive force $H_{CH}$ of the hardened part. The maximum strength is thus selected from the interval 42 shown in the figure. In other words, the varying magnetic field is set, for example, between $$-\frac{H_{CU} + H_{CH}}{2} - \frac{H_{CU} + H_{CH}}{2}.$$

Embodiments, differing from those disclosed above, can also be contemplated within the scope of the invention.

By increasing the amplitude of the magnetization current of the magnetization coil, the magnetic flux can be made to penetrate more deeply in the object being measured, in which case it will be possible to measure greater hardening depths. The magnetic permeability of unhardened steel is generally considerably greater than that of hardened steel. Due to this, the magnetizing flux tends to concentrate in the unhardened layer and the magnetic flux density may then be, for example, twice that of the hardened layer. The magnetic flux density is the primary quantity affecting the dynamics of the elementary domains, so that the concentration of the flux will facilitate the implementation of the measurement method disclosed in the patent.

The MBN sensor 14 used can be, for example, a Hall magnetometer, a coil, or any other kind of sensor, by means of which the strength, magnetic flux, or derivative quantities of these, can be measured. The MBN sensor 14 can also be located differently to the example. The sensor can be, for example, set on the other side of the measurement object, such as a plate, relative to the magnetization coil. The sensor can be placed at different angles and at different points relative to the measurement object, or relative to the points of the magnetization coil.

In a well-protected and designed hardening depth measuring system, disturbances are mainly connected to the sensor through the measurement coil, either magnetically, or capacitively. The greatest magnetic disturbances in measurement are caused by multiples of the frequencies of the power network and magnetization, and the results of their mixing. In order to reduce the multiples of the power network's 50 Hz, the protection must be made carefully and especially must prevent a disturbance from connecting through the magnetization coil to the steel and from there to the measurement coil. Unpaired harmonics connect through the steel most strongly. The filtering of the magnetization current is carried out in the electronics part of the apparatus, so that there is no need to cram space-consuming components into the actual sensor. The cable of the measurement sensor must also be well protected.

Magnetization harmonics are the factor that disturbs most greatly measurements being made at low frequencies. At smaller magnetization frequencies, such as 0.001-1 Hz-magnetization frequencies, the disturbances are less at the 100 Hz measurement frequency. However, the rapid diminishing of the measurement signal limits the reduction of the magnetization frequency.

Variation of the potential of the measurement object relative to the earth potential of the electronics of the sensor causes a capacitively connecting disturbance, because the common-mode attenuation of the preamplifier is finite. In order to reduce the disturbance, the measurement object should be earthed close to the sensor, so that the disturbance currents travelling through the earthing contact will not cause a magnetic field in the signal coil. In order to attenuate disturbances connecting capacitively, the 'centre-point' of the measurement coil can be connected to the earth potential of the sensor's electronics. In other words, the winding wire of the measurement coil is earthed halfway along the wire.

The protective casing of the measurement sensor, the sheathing of the cable, and other casing of the electronics form a common Faraday's protection, which for safety reasons is connected to a protective earth. The earth of the electronics is connected by the preamplifier card to protection at one point. There is a capacitive protection between the primary and secondary windings of the transformer, which is connected to the casing. The preamplifier signal is received in the electronics differentially, or as a current signal.

The magnetization current supply can also be made symmetrical, in order to attenuate capacitive disturbances.

In order to improve the signal-to-noise ratio, the Barkhausen signal can be processed at those times at which a signal is expected. In other words, the MBN will be measured only when the changes in the size of the elementary domains are relatively great.

The method according to the invention can also be used for measuring the hardening depth of other ferro, or ferrimagnetic substances.

It is also possible to apply the method according to the invention to determining other properties, such as the microstructure, composition, or material faults of iron.

The magnetization frequency can be set, for example, between 0-5 Hz, 1-5 Hz, 1-3 Hz. 3-5 Hz, 2-4 Hz, 3-7 Hz, 5-7 Hz, 5-10 Hz, or 4-8 Hz. The magnetization frequency can also be 1.192 Hz, below 10 Hz, below 20 Hz, or below 200 Hz.

The frequency band, above which the MBN signal converted to the frequency level is integrated in order to determine the value depicting the energy of the noise, can be, for example, 200-1200 Hz, 200-1220 Hz, 130-1400 Hz, or 76-1220 Hz. The filters used in the measurement electronics 5 can also be defined to limit the measurement band according to the aforementioned frequency bands, for example, by band-pass filtering the MBN signal according to the aforementioned frequency bands.

The invention claimed is:

1. A method for determining the hardening depth of a ferro or ferrimagnetic measurement object, comprising,
   creating a varying magnetic field in the measurement object,
   regulating the varying magnetic field such that the maximum strength of the magnetic field is at most 110% of a value of a coercitive force of a hardened part of the measurement object,
   measuring Barkhausen noise arising from the varying magnetic field, and originating from the measurement object,
   determining a value representing an energy of the measured noise, and
   determining a hardening depth of the measurement object on the basis of the value representing the energy of the measured noise.

2. A method according to claim 1, wherein the measured Barkhausen noise is converted to the frequency level using a discrete-time Fourier transformation.

3. A method according to claim 2, wherein the value representing the energy of the measured noise is determined by integrating the measured Barkhausen noise converted to the frequency level, over a specific frequency band.

4. A method according to claim 1, wherein the hardening depth of the measurement object is determined on the basis of the value representing the energy of the noise, with the aid of a table or formula, which is defined with the aid of test measurements.

5. A method according to claim 4, wherein the varying magnetic field created in the measurement object is regulated in such a way that the maximum strength of the magnetic field does not exceed the coercitive force of the hardened part of the measurement object, but does exceed the coercitive force of the unhardened part of the measurement object.

6. A method according to claim 4, wherein the magnetic field created in the measurement object is regulated in such a way that the maximum strength of the magnetic field is at most 105% of the value of the coercitive force of the hardened part of the measurement object.

7. A method according to claim 2, wherein
   the measured noise signal is converted to the frequency level using a FFT transformation, and
   a sampling frequency used in measurement and conversion and a frequency of the varying magnetic field created in the measurement object are essentially synchronized with a frequency of a power-supply network, and
   a measurement time is essentially a multiple of the periods corresponding to the frequency of the varying magnetic field created in the measurement object.

8. A method according to claim 1, wherein the frequency of the varying magnetic field created in the measurement object is less than 10 Hz.

9. A method according to claim 1, wherein the frequency of the varying magnetic field created in the measurement object is less than 20 Hz.

10. A method according to claim 1, wherein the Barkhausen noise caused by the varying magnetic field is measured with the aid of a coil sensor, optimized for frequencies of 10 Hz-2 kHz.

11. An arrangement for determining the hardening depth of a ferro or ferrimagnetic measurement object, comprising,
   a magnetization coil for creating a varying magnetic field in the measurement object,
   a sensor for measuring a magnetic Barkhausen noise originating from the measurement object, and caused by the varying magnetic field,
   an apparatus, arranged to determined a value representing an energy of the measured magnetic Barkhausen noise and to determine the hardening depth of the measurement object on the basis of this value, and
   a magnetization circuit arranged to regulate the varying magnetic field created in the measurement object, in such a way that the maximum strength of the magnetic field is at most 110% of the value of a coercitive force of a hardened part of the measurement object.

12. An arrangement according to claim 11, wherein the apparatus is arranged to convert the measured Barkhausen noise to the frequency level using discrete Fourier transformation.

13. An arrangement according to claim 12, wherein the apparatus is arranged to determine the value of the energy of the measured Barkhausen noise by integrating the measured Barkhausen noise converted to the frequency level over a specific frequency band.

14. An arrangement according to claim 11, wherein the apparatus is arranged to determine the hardening depth of the measurement object, on the basis of the value representing the energy of the noise, with the aid of a table or formula, which is defined with the aid of test measurements.

15. An arrangement according to claim 14, wherein the arrangement includes a magnetization circuit arranged to regulate a magnetization current fed to the magnetization coil and the magnetic field created by the magnetization current, a magnetization flux measurement circuit arranged to measure the magnetization flux created by the magnetization coil, with the aid of the coil, and/or a magnetization current measurement arranged to measure the current travelling through the magnetization coil.

16. An arrangement according to claim 15, wherein the apparatus is arranged to regulate the strength of the magnetic field created in the measurement object by the magnetization coil, with the aid of the magnetization circuit, the magnetization flux measurement circuit, and/or the magnetization current measurement circuit, in such a way that the maximum force of the magnetic field does not exceed the coercive force of the hardened part of the measurement object, but does exceed the coercive force of the unhardened part of the measurement object.

17. An arrangement according to claim 15, wherein the apparatus is arranged to regulate the strength of the magnetic field created in the measurement object by the magnetization coil, with the aid of the magnetization circuit, the magnetization flux measurement circuit, and/or the magnetization current measurement circuit, in such a way that the maximum strength of the magnetic field is at most 105% of the value of the coercive force of the hardened part of the measurement object.

18. An arrangement according to claim 15, wherein the apparatus is arranged to regulate the strength of the magnetic field created in the measurement object by the magnetization coil, with the aid of the magnetization circuit, the magnetization flux circuit, and/or the magnetization current circuit, in such a way that the magnetization flux settles to an essentially constant value, independently of the measurement object.

19. An arrangement according to claim 12, wherein the apparatus is arranged to convert the measured noise signal to the frequency level using a FFT transformation, and to use in the conversion a sampling frequency, which is essentially synchronized with a power-supply network frequency and the frequency of the varying magnetic field created in the measurement object, and a measurement time, which is essentially a multiple of the periods corresponding to the frequency of the varying magnetic field created in the measurement object.

20. An arrangement according to claim 15, wherein the apparatus is arranged to regulate the frequency of the magnetic field created in the measurement object by the magnetization coil to less than 10 Hz, with the aid of the magnetization circuit, the magnetization flux measurement circuit, and/or the magnetization current measurement circuit.

21. An arrangement according to claim 15, wherein the apparatus is arranged to regulate the frequency of the magnetic field created in the measurement object by the magnetization coil to less than 20 Hz, with the aid of the magnetization circuit, the magnetization flux measurement circuit, and/or the magnetization current measurement circuit.

22. An arrangement according to claim 11, wherein the sensor is a coil sensor optimized for low frequencies of less than 1-2 kHz.

* * * * *